(12) United States Patent
Rabiner et al.

(10) Patent No.: US 7,842,040 B2
(45) Date of Patent: Nov. 30, 2010

(54) INTERNAL BONE FIXATION SYSTEM WITH INTEGRATED MIXER

(75) Inventors: Robert A. Rabiner, Tiverton, RI (US); Daniel E. Rabiner, Tiverton, RI (US); Raoul I. Rabiner, Perth Amboy, NJ (US); Leo L. Basta, Providence, RI (US)

(73) Assignee: IlluminOss Medical, Inc., East Providence, RI (US)

( * ) Notice: Subject to any disclaimer, the term of this patent is extended or adjusted under 35 U.S.C. 154(b) by 224 days.

(21) Appl. No.: 12/016,641

(22) Filed: Jan. 18, 2008

(65) Prior Publication Data
US 2009/0187192 A1   Jul. 23, 2009

(51) Int. Cl.
*A61B 17/58* (2006.01)
(52) U.S. Cl. .............................. 606/92; 606/93; 606/94
(58) Field of Classification Search .............. 606/92–94, 606/95, 63
See application file for complete search history.

(56) References Cited

U.S. PATENT DOCUMENTS

| | | | | |
|---|---|---|---|---|
| 2,670,938 A * | 3/1954 | Wittmann | .................... | 366/343 |
| 4,294,251 A | 10/1981 | Greenwald et al. | .......... | 128/276 |
| 4,808,184 A * | 2/1989 | Tepic | .......................... | 604/518 |
| 5,554,111 A | 9/1996 | Morrey et al. | ................. | 604/26 |
| 5,707,374 A | 1/1998 | Schmidt | ....................... | 606/85 |
| 6,358,252 B1 | 3/2002 | Shapira | ........................ | 606/80 |
| 6,478,751 B1 | 11/2002 | Krueger et al. | ............... | 600/566 |
| 2004/0049203 A1 * | 3/2004 | Scribner et al. | ............... | 606/93 |
| 2004/0186481 A1 * | 9/2004 | Chern Lin et al. | ............. | 606/92 |
| 2005/0010231 A1 * | 1/2005 | Myers | .......................... | 606/86 |
| 2007/0173939 A1 * | 7/2007 | Kim et al. | ................. | 623/17.11 |

FOREIGN PATENT DOCUMENTS

| | | | | |
|---|---|---|---|---|
| WO | WO 2004/0112661 | | 12/2004 | ................... 17/88 |
| WO | WO 2005/0112804 | | 12/2005 | ................... 17/72 |

\* cited by examiner

*Primary Examiner*—Thomas C Barrett
*Assistant Examiner*—Michael T Schaper
(74) *Attorney, Agent, or Firm*—Greenberg Traurig, LLP; David J. Dykeman; Danielle T. Abramson

(57) ABSTRACT

Systems and methods for repairing a weakened or fractured bone are disclosed herein. A system for repairing a fractured bone includes a delivery catheter having an elongated shaft with a proximal end, a distal end, and a longitudinal axis therebetween, wherein the delivery catheter has an inner void for passage of bone cement components and an inner lumen for passage of a mixing element; an internal bone fixation device releasably engaging the distal end of the delivery catheter, wherein the internal bone fixation device moves from a first compact state to a second expanded state when the bone cement components are delivered to the internal bone fixation device and mixed within the internal bone fixation device; and a spinning mechanism engaged to a rotatable shaft, wherein the spinning mechanism is inserted into the internal bone fixation device.

20 Claims, 7 Drawing Sheets

INTERNAL BONE FIXATION SYSTEM WITH INTEGRATED MIXER

RELATED APPLICATIONS

None.

FIELD

The embodiments disclosed herein relate to systems for repairing a weakened or fractured bone, and more particularly to systems that include internal bone fixation devices having bone cement components that are mixed together and cured within the internal bone fixation device in situ and methods of using these systems for repairing a weakened or fractured bone.

BACKGROUND

Fracture repair is the process of rejoining and realigning broken bones. Fracture repair is required when there is a need for restoration of the normal position and function of the broken bone. Throughout the stages of fracture healing, the bones must be held firmly in the correct position and supported until it is strong enough to bear weight. In the event the fracture is not properly repaired, malalignment of the bone may occur, resulting in possible physical dysfunction of the bone or joint of that region of the body.

The addition of bone cements or other compounds to a fractured bone for repairing bone and, for example, joining bones are known in the art and typically requires at least two steps. Conventional bone cement injection devices are similar to a household caulking gun. Typically, the injection device has a pistol-shaped body, which supports a cartridge containing the bone cement. Bone cements are usually found as two component systems (powder and liquid) and must be mixed in a mixer and transferred into the cartridge for injection. In conventional bone cement mixers, the mixing element or stirrer is inserted into the mixing vessel after the bone cement powder and monomer liquid have been placed in the vessel. When mixing is complete, the stirrer is withdrawn from the cement and the cement is manually transferred from the mixing vessel to the injection device. Stirrer withdrawal from the cement exposes a large surface area of the cement to room air and undesirably introduces significant amounts of monomer liquid vapor in the ambient air. This process is unpleasant for individuals mixing the cement, since the mixed cement often contains an offensive, noxious odor. Furthermore, removal of the mixed cement from the mixing vessel into the cartridge of the injection device is cumbersome, time consuming, and has the potential for being mishandled and/or dropped.

Once the bone cement has been added to the cartridge of the injection device, the bone cement is delivered to the site of the bone fracture. Because the bone cement may be quite thick and viscous, delivering the bone cement from the injection device often requires a great deal of effort applied to the device plunger. Thus, both strength and dexterity are required on the part of the medical professional performing the procedure. The bone cement itself may cause complications including the leakage of the bone cement to an area outside of the fractured bone site, which can result in soft tissue damage as well as nerve root pain and compression. Other reported complications include pulmonary embolism, respiratory and cardiac failure, and death.

Thus, there is a need in the art for devices that can be used to repair a weakened or fractured bone in an effective, efficient and safe manner.

SUMMARY

Systems and methods for repairing a weakened or fractured bone are disclosed herein. According to aspects illustrated herein, there is provided a system for repairing a fractured bone that includes a delivery catheter having an elongated shaft with a proximal end, a distal end, and a longitudinal axis therebetween, wherein the delivery catheter has an inner void for passage of bone cement components and an inner lumen for passage of a mixing element; an internal bone fixation device releasably engaging the distal end of the delivery catheter, wherein the internal bone fixation device moves from a first compact state to a second expanded state when the bone cement components are delivered to the internal bone fixation device and mixed within the internal bone fixation device; and a spinning mechanism engaged to a rotatable shaft, wherein the spinning mechanism is inserted into the internal bone fixation device.

According to aspects illustrated herein, there is provided a method for repairing a fractured bone that includes gaining access to an inner cavity of the fractured bone; providing a system for use in repairing the fractured bone, the system comprising an internal bone fixation device releasably engaging a delivery catheter, the internal bone fixation device housing a powder component of a bone cement; positioning the internal bone fixation device spanning at least two bone segments of the fractured bone; adding a liquid component of the bone cement to the internal bone fixation device by passage through an inner void of the device; inserting the mixing element through the delivery catheter and into the internal bone fixation device; activating the mixing element to mix the powder component and the liquid component of the bone cement within the internal bone fixation device, wherein the internal bone fixation device moves from a first compact state to a second expanded state; removing the mixing element from the device; waiting for the mixed bone cement to cure, wherein the curing of the bone cement results in a hardened internal bone fixation device; and releasing the hardened internal bone fixation device from the delivery catheter.

According to aspects illustrated herein, there is provided a method for repairing a fractured bone that includes gaining access to an inner cavity of the fractured bone; providing a system for use in repairing the fractured bone, the system comprising an internal bone fixation device releasably engaging a delivery catheter, the internal bone fixation device housing a powder component of a bone cement; positioning the internal bone fixation device spanning at least two bone segments of the fractured bone; adding a liquid component of the bone cement to the internal bone fixation device by passage through an inner void of the device; inserting a mixing element through the delivery catheter and into the internal bone fixation device, the mixing element comprising a spinning mechanism releasably engaging a rotatable shaft; activating the mixing element to mix the powder component and the liquid component of the bone cement within the internal bone fixation device, wherein the internal bone fixation device moves from a first compact state to a second expanded state; releasing the spinning mechanism from the rotatable shaft; removing the rotatable shaft from the device; waiting for the mixed bone cement to cure, wherein the curing of the bone cement results in a hardened rebar-enforced internal bone fixation device; and releasing the hardened rebar-enforced internal bone fixation device from the delivery catheter.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 3A shows a perspective view of a distal end of the system. FIG. 3B shows a cross-sectional view of the system taken along line B-B of FIG. 3A.

FIG. 6A shows an expandable body in a compact state. FIG. 6B shows the expandable body in an expanded state, after a two-component bone cement has been added, mixed and hardened in situ.

Figure 1:
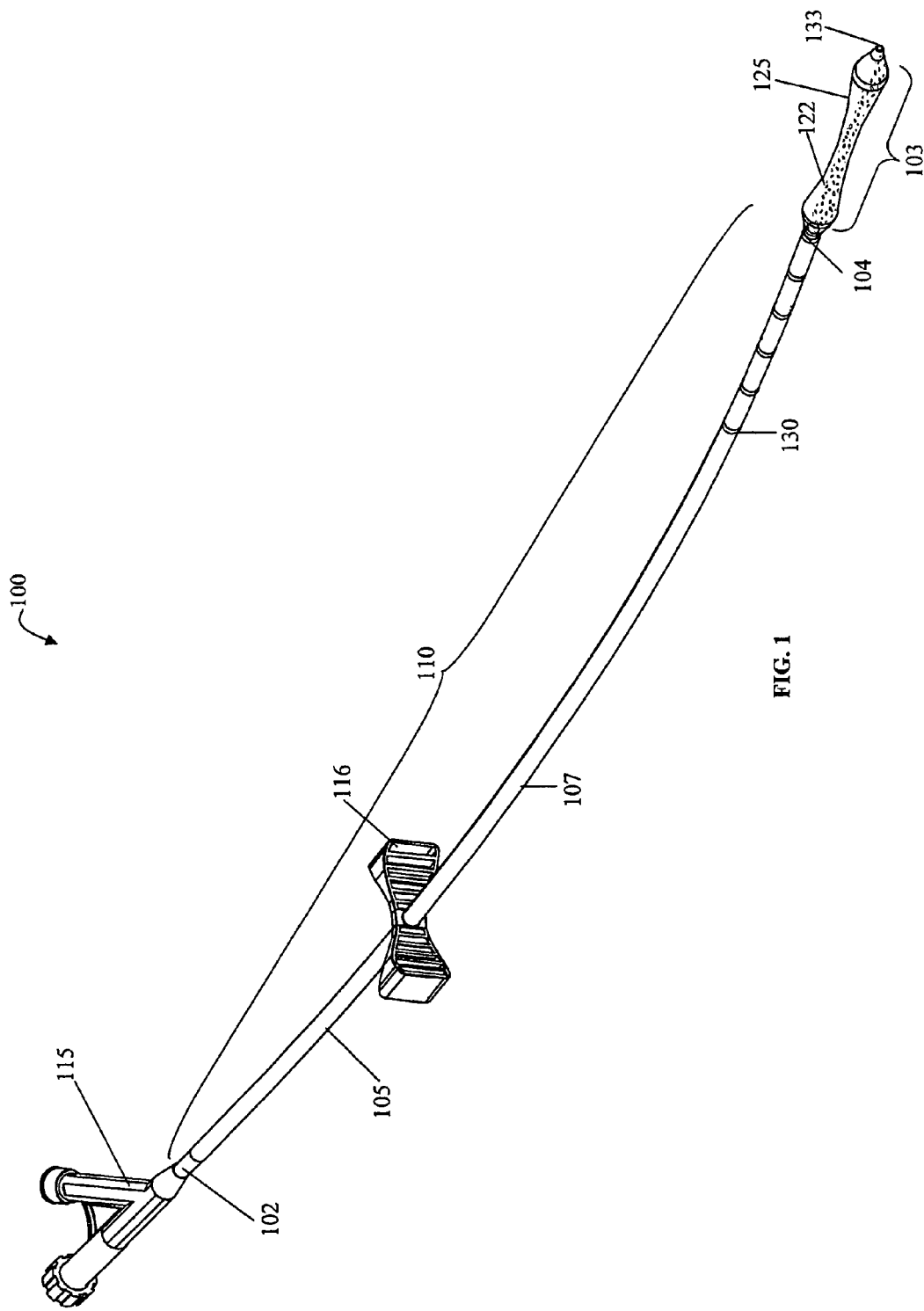
FIG. 1 shows a perspective view of a system for repairing a weakened or fractured bone of the presently disclosed embodiments.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for repairing weakened or fractured bones are disclosed herein. The systems disclosed herein include an internal bone fixation device that is an expandable body. A powder component of a bone cement is contained within the expandable body. During a procedure for repairing a fractured bone, an internal bone fixation device of the system is placed within an inner cavity of a fractured bone. Once in place, a liquid component of the bone cement is added to the powder-filled internal bone fixation device. A mixing element is then passed through an inner lumen of a delivery catheter that is engaged to the internal bone fixation device. The two components of the bone cement are uniformly mixed in the internal bone fixation device in situ. The fully mixed bone cement subsequently goes through a curing cycle and is hardened within the internal bone fixation device. The hardened internal bone fixation device may then be released from the delivery catheter and sealed to enclose the cured bone cement within the internal bone fixation device. The hardened internal bone fixation device remains within the inner cavity of the fractured bone and provides support and proper orientation of the fractured bone resulting in the repair, healing, and strengthening of the fractured bone. The systems for repairing a weakened or fractured bone disclosed herein provide many advantages over known systems including, but not limited to, minimizing the amount of air bubbles in the mixed bone cement, minimizing the release of monomer liquid vapor to the air, reducing the cumbersome step of moving the bone cement from a mixer to an injection device, avoiding the difficulties encountered when trying to push a fully mixed bone cement through an injection device, and minimizing the amount of bone cement that leaks out to surrounding bone and tissues.

In an embodiment, a two-component bone cement is a powder/liquid system based on a polyacrylic cement (a polymethacrylic cement) or a calcium phosphate cement (CPC). In an embodiment, the two-component bone cement is PolyMethylMethAcrylate (PMMA). PMMA is supplied as a polymethylmethacrylate (PMMA) powder and a liquid methyl methacrylate (MMA). When mixed these yield a dough-like cement that gradually hardens. In an embodiment, the PMMA bone cement is a non-absorbable bone cement, such as Surgical Simplex P, Palacost R, Zimmer Regular, Zimmer Low Viscosity (LVC), CMW-I, CMW-3, Osteopal®, Osteobond®, Endurance™ bone cement, or a similar product. In an embodiment, the bone cement may be a non-absorbable PMMA bone cement with antibiotics, such as Palacos® R with gentamycin, Surgical Simplex P with tobramycin, or a similar product. The bone cement may be an absorbable product, such as Norian SRS®, calcium phosphate cement (CPC), calcium phosphate hydraulic cement (CPHC), sodium citrate modified calcium phosphate cement, hydroxyapatite (HA) cement, hydroxyapatite calcium phosphate cements (CPCs); a beta-TCP-MCPM-CSH cement [beta-tricalcium phosphate (beta-TCP), monocalcium phosphate monohydrate (MCPM), and calcium sulfate hemihydrate (CSH)]; a bioactive bone cement (GBC) with bioactive $MgO-CaO-SiO_2-P_2O_5-CaF_2$ glass beads and high-molecular-weight polymethyl methacrylate (hPMMA); a tricalcium phosphate (TCP), tetracalcium phosphate (TTCP), and dicalcium phosphate dehydrate (DCPD) bone cement with dense TCP granules; an hPMMA with delta- or alpha-alumina powder (delta-APC or alpha-APC); a similar product; or any other material that provides sufficient strength upon hardening. In an embodiment, the two-component bone cement is a calcium phosphate two component apatitic cement composition. In an embodiment, the two-component bone cement is a polyurethane material. Those skilled in the art will recognize that the mixing element and delivery catheter of the presently disclosed embodiments are compatible with all types of bone cement. Furthermore, the devices of the presently disclosed embodiments are equally effective with all viscosity bone cements, thereby enabling a single device to be employed for any bone cement, ranging from low viscosity cements to high viscosity cements. In addition, vacuum may be used, if desired, thereby further expanding the range of products with which the devices may be employed.

Several epoxies known in the art are suitable for use as bone cements and vary in viscosity, cure times, and hardness (durometer or shore) when fully cured. A durometer of a material indicates the hardness of the material, defined as the material's resistance to permanent indentation. Depending on the amount of resultant support that is necessary for a given bone fracture, a specific durometer bone cement may be chosen. The durometer of a material may be altered to achieve either greater rigidity or a more malleable result. The mechanical properties of the bone cement may dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

A system disclosed herein may be used for the repair of bones that have weakened or fractured due to any of the bone diseases including, but not limited to osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, scoliosis, and other similar diseases. A system disclosed herein may be used for the repair of bones that have weakened or fractured due to an injury, for example, a fall. A device disclosed herein may be used during a percutaneous vertebroplasty or kyphoplasty procedure.

Figure 2:
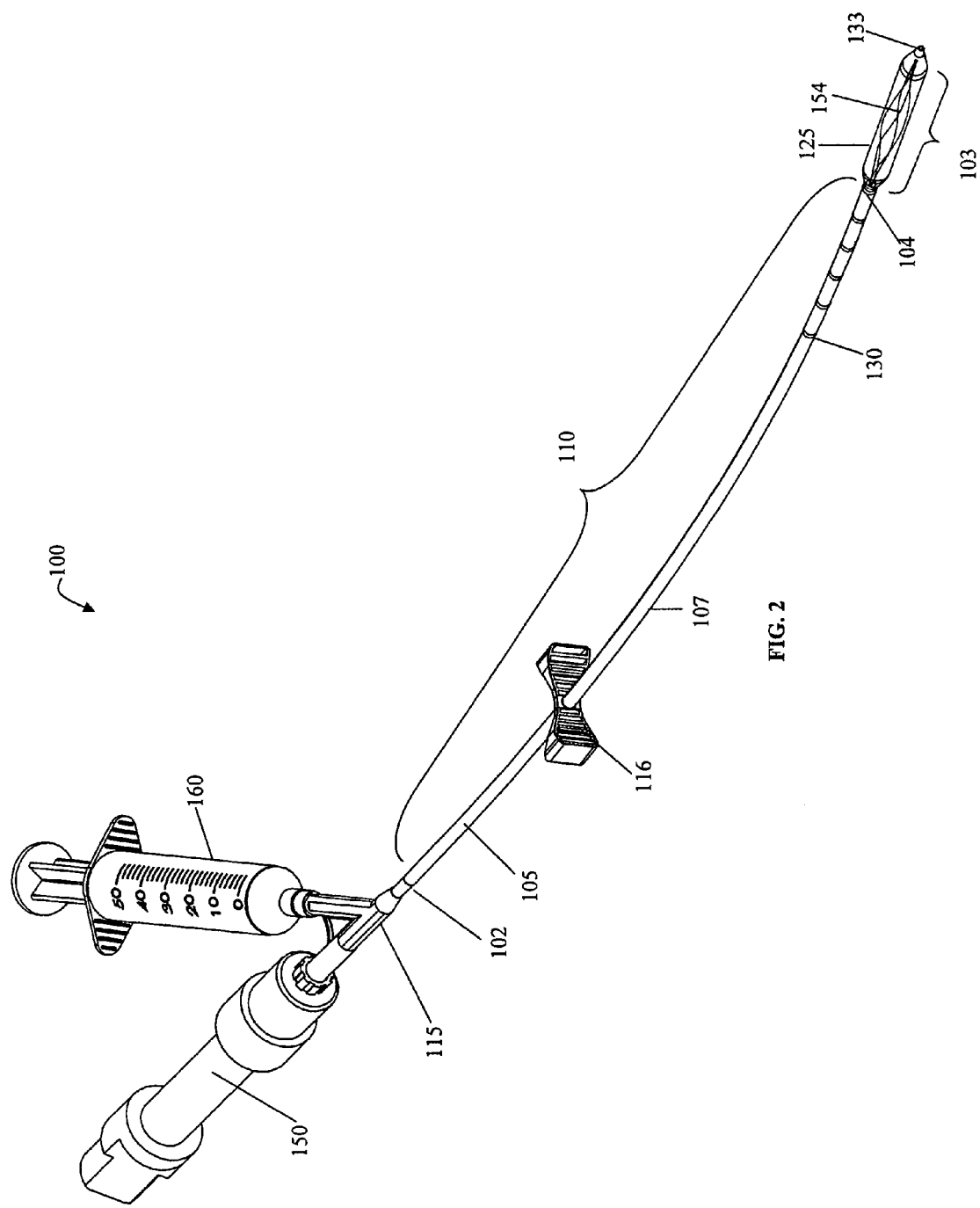
FIG. 2 shows a perspective view of a system for repairing a weakened or fractured bone of the presently disclosed embodiments.

The main components of a system 100 for repairing a weakened or fractured bone are shown generally in FIG. 1 in conjunction with FIG. 2. The system 100 includes a delivery catheter 110 having an elongated shaft with a proximal end 102, a distal end 104, and a longitudinal axis therebetween. In an embodiment, the delivery catheter 110 has a diameter of about 3 mm. The distal end 104 of the delivery catheter 110 terminates in an expandable body 103. The expandable body 103 is made from a pliable, resilient, conformable, biocompatible, and strong material. The expandable body 103 may be referred to as an internal bone fixation device (IBFD). As shown in FIG. 1 the expandable body 103 comprises a powder component 122 of a two-component bone cement. The expandable body 103 is able to move from a first compact position to a second expanded position when a liquid component of the two-component bone cement is delivered to the expandable body 103. In an embodiment, the expandable body 103 has a compact diameter of about 2.5 mm. In an embodiment, the expandable body 103 has an expanded diameter ranging from about 4 mm to about 9 mm. The powder and/or liquid components of the two-component bone cement may be delivered to the expandable body 103 via an inner void capable of allowing the components to pass through. The powder component 122 of the bone cement may be pre-loaded in the expandable body 103 or may be added to the expandable body 103 by injection, suction (using a vacuum) or other methods known in the art.

The expandable body 103 may be round, flat, cylindrical, oval, rectangular or another shape. The expandable body 103 may be formed from a material, including but not limited to, urethane, polyethylene terephthalate (PET), nylon elastomer and other similar polymers. In an embodiment, the expandable body 103 is constructed out of a PET nylon aramet or other non-consumable materials. PET is a thermoplastic polymer resin of the polyester family that is used in synthetic fibers. Depending on its processing and thermal history, PET may exist both as an amorphous and as a semi-crystalline material. Semi-crystalline PET has good strength, ductility, stiffness and hardness. Amorphous PET has better ductility, but less stiffness and hardness. PET can be semi-rigid to rigid, depending on its thickness, and is very lightweight. PET is strong and impact-resistant, naturally colorless and transparent and has good resistance to mineral oils, solvents and acids.

In an embodiment, the expandable body 103 is designed to evenly contact an inner wall of a cavity in a fractured bone. In an embodiment, the expandable body 103 may have a pre-defined shape to fit inside the cavity in a particularly shaped bone. For example, as depicted in the embodiment of FIG. 1, the pre-defined shape of the expandable body 103 may be an elongated cylinder. The expandable body 103 has an outer surface 125. In an embodiment, the outer surface 125 of the expandable body 103 is substantially even and smooth and substantially mates with a wall of the cavity in the bone. In an embodiment, the outer surface 125 of the expandable body 103 is not entirely smooth and may have some small bumps or convexity/concavity along the length. In some embodiments, there are no major protuberances jutting out from the outer surface 125 of the expandable body 103. The expandable body 103 may be designed to remain within the cavity of the bone and not protrude through any holes or cracks in the bone. In an embodiment, the outer surface 125 of the expandable body 103 may be flush with the wall of the cavity and when the expandable body 103 is expanded, the outer surface 125 may contact the wall of the cavity along at least a portion of the surface area. In an embodiment, when the expandable body 103 is expanded, a majority or all of the body's 103 outer surface 125 does not contact the wall of the cavity and does not extend through any holes or cracks in the bone.

The outer surface 125 of the expandable body 103 may be coated with materials such as drugs, bone glue, proteins, growth factors, antibiotics, or other coatings. For example, after a minimally invasive surgical procedure an infection may develop in a patient, requiring the patient to undergo antibiotic treatment. An antibiotic drug may be added to the outer surface 125 of the expandable body 103 to prevent or combat a possible infection. Proteins, such as, for example, the bone morphogenic protein or other growth factors have been shown to induce the formation of cartilage and bone. A growth factor may be added to the outer surface 125 of the expandable body 103 to help induce the formation of new bone. Due to the lack of thermal egress of the bone cement in the expandable body 103, the effectiveness and stability of the coating is maintained.

In an embodiment, the outer surface 125 of the expandable body 103 may have ribs, ridges, bumps or other shapes to help the expandable body 103 conform to the shape of a bone cavity. The expandable body 103 may be constructed to achieve transit within luminal cavities of bones and to expand, manipulate, and remove obstructions. In this way, the expandable body 103 may slide easier within the luminal bodies without coming in contact with surrounding tissue. The expandable body 103 may also be designed to be placed in a bone and to grab a fractured bone without any slippage using a textured surface with a variety of shapes such as small ridges or ribs.

In an embodiment, a water soluble glue is applied to the outer surface 125 of the expandable body 103. When the expandable body 103 is expanded and engages a moist bone, the water soluble glue on the outer surface 125 of the expandable body 103 becomes sticky or tacky and acts as a gripping member to increase the conformal bond of the expandable body 103 to the bone. Once the expandable body 103 is expanded, the outer surface 125 of the expandable body 103 grips the bone forming a mechanical bond as well as a chemical bond. These bonds prevent the potential for a bone slippage. The water soluble glue may be cured by any light (e.g., UV not required).

In an embodiment, the expandable body 103 has a textured surface which provides one or more ridges that allow grabbing all portions of bone fragments of a fractured bone. In an embodiment, ridges are circumferential to the expandable body 103 and designed to add more grab to the inflated expandable body 103 on contact with the fractured bone. The ridges are also compressive so the ridges fold up on the fractured bone when the expandable body 103 is completely inflated. In an embodiment, sand blasted surfacing on the outer surface 125 of the expandable body 103 improves the connection and adhesion between the outer surface 125 of the expandable body 103 and the inner bone. The surfacing significantly increases the amount of surface area that comes in contact with the bone resulting in a stronger grip.

The expandable body 103 of the system 100 typically does not have any valves. One benefit of having no valves is that the expandable body 103 may be inflated or deflated as much as necessary to assist in the fracture reduction and placement. Another benefit of the expandable body 103 having no valves is the efficacy and safety of the system 100. Since there is no communication passage of bone cement to the body there cannot be any leakage of the bone cement because all the cement is contained within the expandable body 103. In an embodiment, a permanent seal is created between the expandable body 103 that is both hardened and affixed prior to the delivery catheter 110 being removed. The expandable body 103 may have valves, as all of the embodiments are not intended to be limited in this manner.

The expandable body 103 of the system 100 has a diameter ranging from about 5 mm to about 9 mm. The expandable body 103 of the system 100 has a length ranging from about 20 mm to about 80 mm. In an embodiment, the expandable body 103 has a diameter of about 5 mm and a length of about 30 mm. In an embodiment, expandable body 103 has a diameter of about 5 mm and a length of about 40 mm. In an embodiment, the expandable body 103 has a diameter of about 6 mm and a length of about 30 mm. In an embodiment, the expandable body 103 has a diameter of about 6 mm and a length of about 40 mm. In an embodiment, the expandable body 103 has a diameter of about 6 mm and a length of about 50 mm. In an embodiment, the expandable body 103 has a diameter of about 7 mm and a length of about 30 mm. In an embodiment, the expandable body 103 has a diameter of about 7 mm and a length of about 40 mm. In an embodiment, the expandable body 103 has a diameter of about 7 mm and a length of about 50 mm.

In an embodiment, a stiffening member 105 surrounds the elongated shaft of the delivery catheter 110 and provides rigidity over the elongated shaft 101. In an embodiment, a pusher or stabilizer 116 is loaded proximal to the expandable body 103. In an embodiment, a slip sleeve 107 surrounds the stiffening member 105. In an embodiment, the slip sleeve 107 surrounds the stiffening member 105 from the proximal end 123 of the expandable body 103 up until the pusher 116. One or more radiopaque markers or bands 130 may be placed at various locations along the expandable body 103 and/or the slip sleeve 107. A radiopaque ink bead 133 may be placed at the distal end 121 of the expandable body 103 for alignment of the system 100 during fluoroscopy. The one or more radiopaque bands 130, using radiopaque materials such as barium sulfate, tantalum, or other materials known to increase radiopacity, allows a medical professional to view the system 100 using fluoroscopy techniques. The one or more radiopaque bands 130 also provide visibility during inflation of the expandable body 103 to determine the precise positioning of the expandable body 103 and the system 100 during placement and inflation. The one or more radiopaque bands 130 permit visualization of any voids that may be created by air that gets entrapped in the expandable body 103. The one or more radiopaque bands 130 permit visualization to preclude the expandable body 103 from misengaging or not meeting the bone due to improper inflation to maintain a uniform member/bone interface.

In an embodiment, an adapter 115, such as a Tuohy-Borst adapter, engages the proximal end 102 of the delivery catheter 110. A mixing element 150 may be introduced into one of the side-arms of the adapter 115 and passes within an inner lumen of the delivery catheter 110 up until the distal end 104 of the delivery catheter 110. The mixing element 150 is movable within the expandable body 103. The mixing element 150 mixes the powder and liquid components of the bone cement together in situ to form a flowable bone cement. A bone cement injection system 160 housing the powder and/or the liquid components of the bone cement may be introduced into another side-arm of the adapter 115. Alternately, a Luer fitting may engage the proximal end 102 of the delivery catheter 110 and a Luer fitting would exist on the mixing element 150 such that the delivery catheter 110 and the mixing element 150 would lock together.

Examples of bone cement injection systems 160 include, but are not limited to, caulking gun type systems and syringe systems. In the embodiment shown in FIG. 2, the bone cement injection system is a syringe 160. In an embodiment, the syringe 160 has a control mechanism that regulates the flow of the liquid component. The control mechanism of the syringe 160 allows the liquid component to flow into the delivery catheter 110 and the flow may be stopped if desired. The syringe 160 makes direct contact to control the directional flow of the liquid component, and the direction of flow of the liquid component instantaneously changes within the delivery catheter 110 in response to a change in the direction of the syringe 160. The liquid component has a viscosity as measured in Centipoise (cP), the unit of dynamic viscosity, so the liquid component may be infused from the syringe 160 into the delivery catheter 110 and into the expandable body 103.

In an embodiment, a separation area is located at the junction between the distal end 123 of the expandable body 103 and the elongated shaft of the delivery catheter 110. The separation area may have a stress concentrator. The stress concentrator may be a notch, groove, channel or similar structure that concentrates stress in the separation area. The stress concentrator of the separation area may be notched, scored, indented, pre-weakened or pre-stressed to direct separation of the expandable body 103 from the elongated shaft of the delivery catheter 110 under specific torsional load. The separation area ensures that there are no leaks of the bone cement from the elongated shaft of the delivery catheter and/or the expandable body. The separation area seals the expandable body and removes the elongated shaft of the delivery catheter by making a break at a known or predetermined site (e.g., a separation area). The separation area may be various lengths and up to about an inch long. In an embodiment, when torque (twisting) is applied to the delivery catheter 110, the elongated shaft 101 separates from the expandable body 103. The twisting creates a sufficient shear to break the residual bone cement and create a clean separation of the body/shaft interface. In an embodiment, the expandable body 103 is cut from the delivery catheter 110 using a cutting device.

Figure 3A:
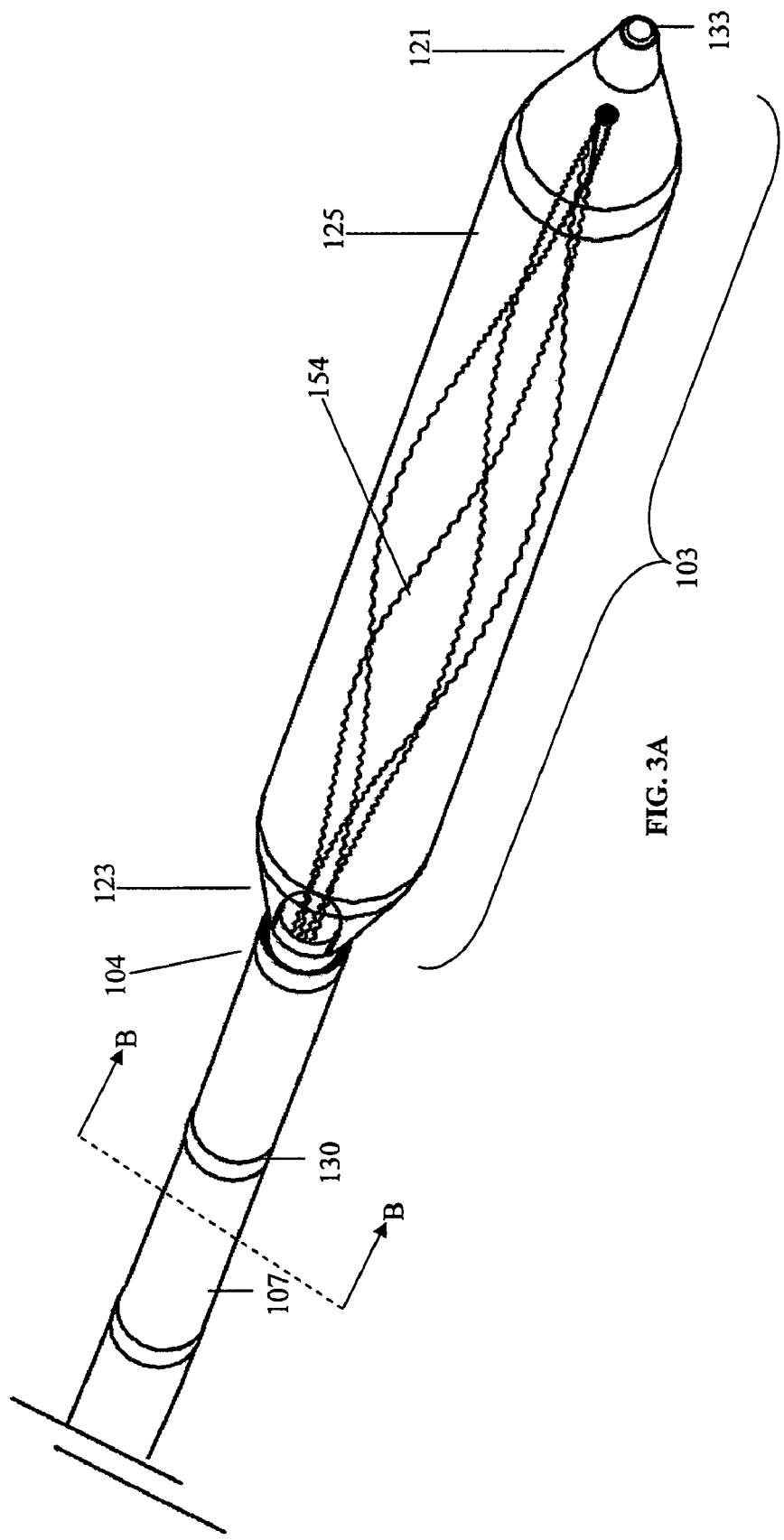
FIG. 3A and FIG. 3B show close-up views of some of the main components of a system for repairing a weakened or fractured bone of the presently disclosed embodiments.
Figure 3B:
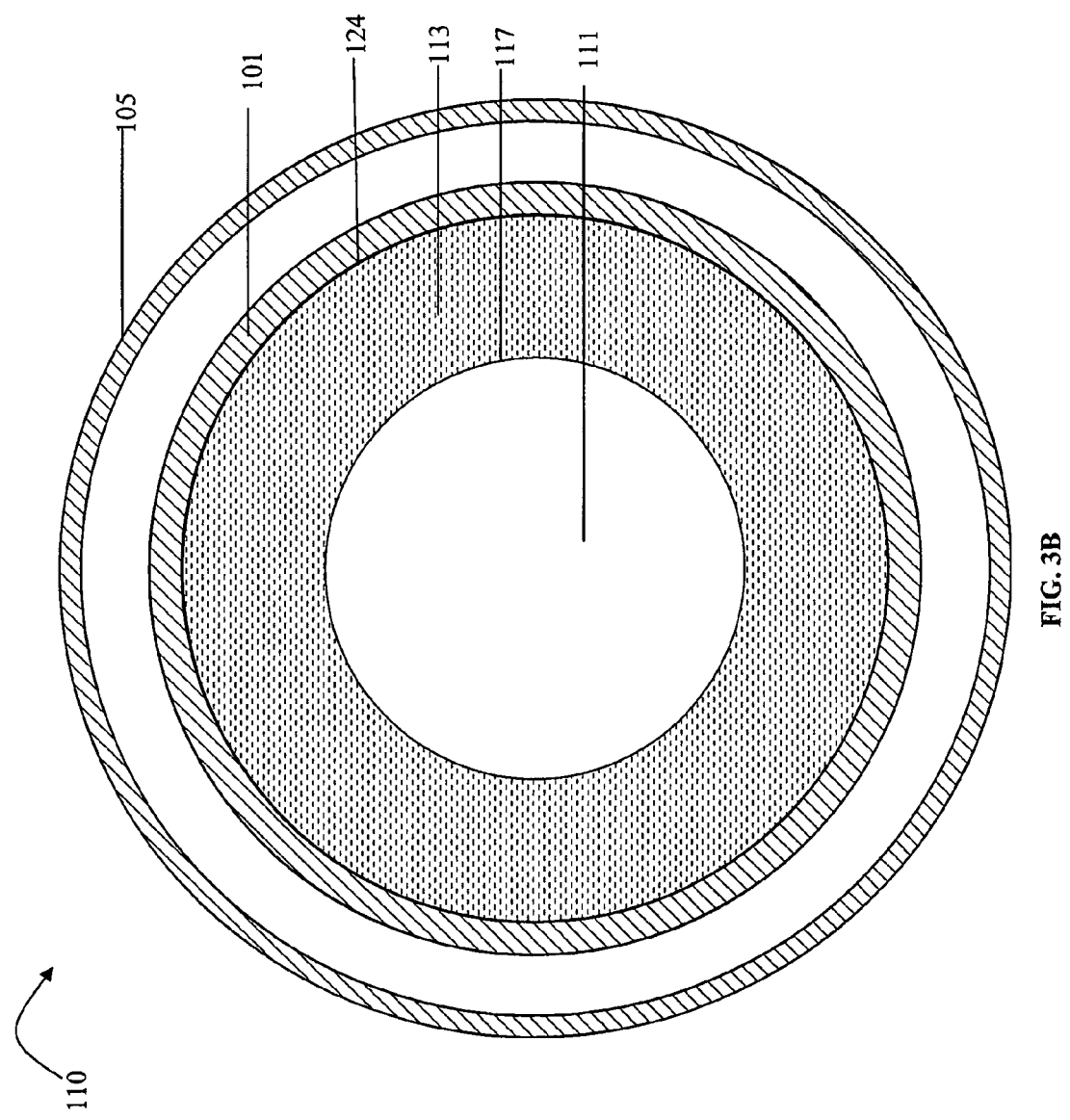

FIG. 3A and FIG. 3B show close-up views of some of the main components of the system 100. As shown in FIG. 3A, one or more radiopaque markers or bands 130 are placed at various locations along the slip sleeve 107 of the system 100. Those skilled in the art will recognize that radiopaque markers 130 may also be placed at various locations along the expandable body 103. In an embodiment, the one or more radiopaque bands 130 are placed at intervals of about 10 mm along the length of the slip sleeve 107. In an embodiment, a radiopaque ink bead 133 is placed at the distal end 121 of the expandable body 103 for easy visualization and alignment of the system 100 by fluoroscopy during a repair procedure. The radiopaque markers 130 and radiopaque ink bead 133 are formed using radiopaque material such as barium sulfate, tantalum, or other materials known to increase radiopacity. The radiopaque markers 130 provide visibility during inflation of the expandable body 103 to determine the precise positioning of the expandable body 103 and the delivery catheter 110 during placement and inflation. The radiopaque markers 130 permit visualization of voids created by air that may be entrapped in the expandable body 103. The radiopaque markers 130 permit visualization to preclude the expandable body 103 from misengaging or not meeting the surface of a bone due to improper inflation. Once the correct positioning of the expandable body 103 and delivery catheter 110 are determined, the proximal end of the delivery catheter 110 may be attached to a delivery system that contains a bone cement.

A cross-sectional view taken along line B-B of FIG. 3A is shown in FIG. 3B. For simplicity, the mixing element 150 has not been shown. As shown in FIG. 3B, the stiffening member 105 surrounds and provides rigidity to the elongated shaft of the delivery catheter 110. The outer slip sleeve 107 has not been shown in this figure. The mixing element conduit 111 provides a space for the mixing element 150 to pass through. The inner void 113 for passage of the bone cement components is formed between the outer surface 117 of the mixing element conduit 111 and the inner surface 124 of the delivery catheter 110. The outer surface 117 of the mixing element conduit 111 allows for a separation between the mixing element and the bone cement components within the elongated shaft 101 of the deliver catheter 110.

Figure 4:
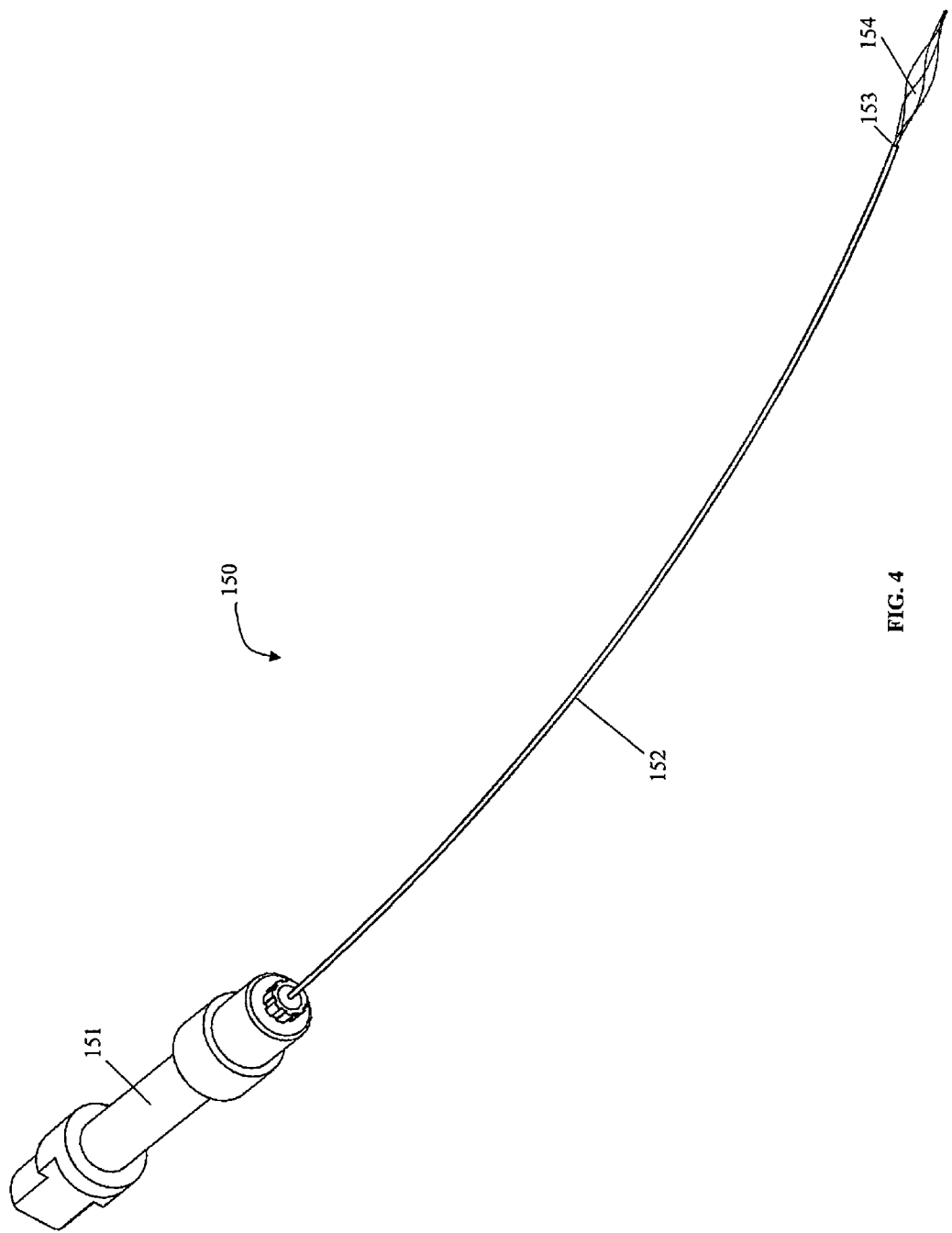
FIG. 4 shows a perspective view of a mixing element of a system for repairing a weakened or fractured bone of the presently disclosed embodiments.

FIG. 4 in conjunction with FIG. 2 shows a mixing element 150 for use with the system 100 of the presently disclosed embodiments. The mixing element 150 is used to mix the two-component bone cement within the expandable body 103 in situ. The mixing element 150 includes a handle 151 attached to a rotatable shaft 152 that terminates in a spinning mechanism 154. The spinning mechanism 154 may be disposable or designated for single-use only. The spinning mechanism 154 may comprise a wire, a fin, a plug, a burr, a blade or any other spinner known in the art. The shape of the spinning mechanism 154 may include a propeller, an egg beater, a sinusoidal wire or any other shape known in the art. The spinning mechanism 154 may be any shape and size, depending upon the particular use and the size and shape of the IBFD 100 to be used. For various uses, the shape may be ovoid, spherical, ellipsoidal, cylindrical, cubical, prismatic, spool-shaped, bell-shaped, a combination of these shapes, or an amorphous shape. The spinning mechanism 154 mixes the components of the bone cement in the expandable body 103 in situ until a certain viscosity is reached. For example, if the spinning mechanism 154 is a propeller, a sensor on the propeller can monitor the drag on the propeller and determine when a certain viscosity has been reached and the pressure is maintained in the expandable body 103. The rotatable shaft 152 may be attached to a drive mechanism including, but not limited to, an electric motor, battery powered, pneumatic or other power source engaged to the handle 151. If the drive mechanism is a motor, a sensor on the motor can monitor the drag on the spinning mechanism 154 and determine when a certain viscosity has been reached and the pressure is maintained in the expandable body 103. The mixing element 150 may be set to stir the two-component bone cement for a predetermined time or until a certain viscosity is reached, which will cause the propeller to stop. In an embodiment, the mixing of the bone cement occurs under vacuum.

In certain situations, it is desirable to use a mixing element 150 that includes a handle 151 attached to a rotatable shaft 152 that terminates in a releasable spinning mechanism 154. The spinning mechanism 154 may be disengaged from the rotatable shaft 152 by various techniques including, but not limited to, the presence of a stress concentrator at a separation area on the mixing element 150, by use of an active release mechanism or by unscrewing the rotatable shaft 152 from the spinning mechanism 154. Other means of removing the spinning mechanism 154 from the rotatable shaft 152 are envisioned and fall within the scope and spirit of the presently disclosed embodiments. If the spinning mechanism 154 is disengaged from the mixing element 150 and remains within the IBFD 100 during healing, the combination of the expandable body 103, the hardened bone cement, and the spinning mechanism 154, function as a rebar-enforced IBFD and provide extra strength and support to the fractured bone during the healing process.

In an embodiment, a separation area 153 is located at the junction between a distal end of the rotatable shaft 152 and a proximal end of the spinning mechanism 154. The separation area 153 includes a stress concentrator in the form of a notch, groove, channel or similar structure that concentrates stress in the separation area 153. The stress concentrator of the separation area 153 may be notched, scored, indented, pre-weakened or pre-stressed to direct separation of the spinning mechanism 154 from the rotatable shaft 152 under specific torsional load. The separation area 153 removes the rotatable shaft 152 of the mixing element 150 by making a break at a known or predetermined site (e.g., a separation area). The separation area may be various lengths and up to about an inch long. In an embodiment, when torque (twisting) is applied to the mixing element 150, the rotatable shaft 152 separates from the spinning mechanism 154. The twisting creates a sufficient shear to create a clean separation of the stirrer/shaft interface. In an embodiment, the spinning mechanism 154 is released from the rotatable shaft 152 by use of an active release mechanism. Once actuated, the active release mechanism will disengage the stirrer from the shaft.

In an embodiment, the mixing element 150 includes a rotatable shaft 152 configured to vibrate. In an embodiment, the rotatable shaft 152 may be a thin, flexible, wire-like body that vibrates all along the length of the rotatable shaft 152. In an embodiment, the rotatable shaft 152 may be attached to an electric motor for powering the vibration of the mixing element 150. The electric motor may include a piezoelectric element that is able to convert current into an ultrasonic vibration. The frequency of vibration of the mixing element 150 may be selected for the desired viscosity of the bone cement mixture, and need not be in the ultrasonic range. Likewise, the amplitude of the vibrations created by the mixing element 150 may vary according to the desired viscosity of the bone cement mixture. In an embodiment, the desired viscosity of the bone cement mixture may include a controller coupled to the motor whereby the user may vary the frequency and amplitude of the vibration.

The mixing element 150 is introduced into a side arm of the adapter 115 that engages the proximal end 102 of the delivery catheter 110. The mixing element 150 runs through the elongated shaft of the delivery catheter 110 through the mixing element conduit and up into the proximal end 123 of the expandable body 103, as shown in FIG. 2.

In an embodiment, carbon nanotubes (CNTs) are added to the bone cement to increase the strength of the material. Carbon nanotubes are an allotrope of carbon that take the form of cylindrical carbon molecules and have novel strength properties. Carbon nanotubes exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the reinforcing materials.

In an embodiment, a fracture repair process reinforces a weakened or fractured bone without exposing the bone through a traditional surgical incision. The presently disclosed embodiments use a minimally invasive approach by making a minor incision to gain access to the bone. Minimally invasive refers to surgical means, such as microsurgical, endoscopic or arthroscopic surgical means, that can be accomplished with minimal disruption of the pertinent musculature, for instance, without the need for open access to the tissue injury site or through minimal incisions. Minimally invasive procedures are often accomplished by the use of visualization such as fiber optic or microscopic visualization, and provide a post-operative recovery time that is substantially less than the recovery time that accompanies the corresponding open surgical approach. Benefits of minimally invasive procedures include causing less trauma because there is minimal blood loss, a reduction in surgery and anesthetized time, shortened hospitalization, and an easier and more rapid recovery. In an embodiment, a bone fixator may be placed within an intramedullary cavity of a weakened or fractured bone. By restoring and preserving bone structure, some of the presently disclosed embodiments permit additional future treatment options.

Figure 5:
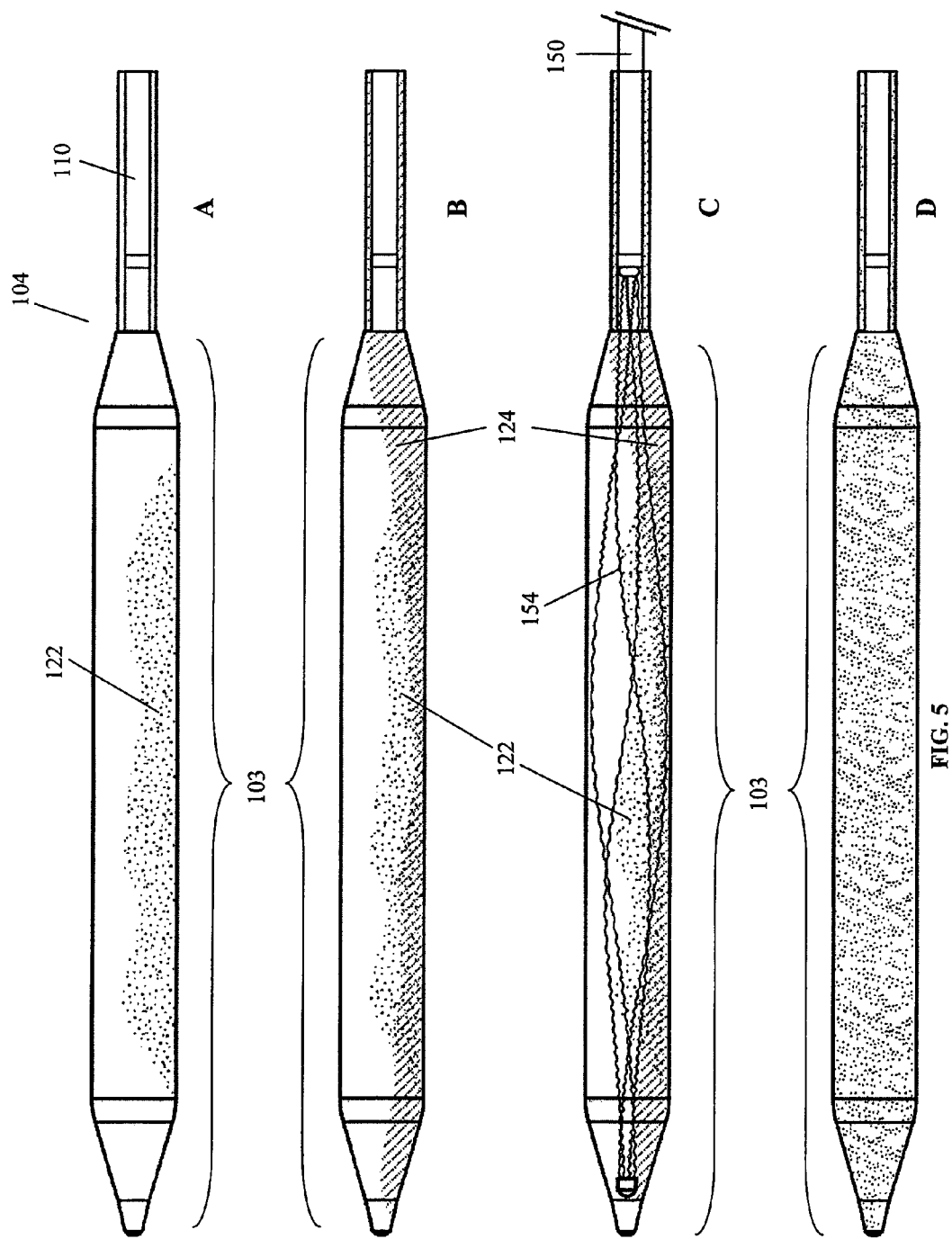
FIG. 5 shows close-up views of a distal end of a system for repairing a weakened or fractured bone of the presently disclosed embodiments. The various method steps showing an exemplary embodiment of a two-component bone cement being mixed within an expandable body in situ, are shown in FIG. 5A-D.

FIG. 5 illustrates close-up views of the distal end 104 of the system for repairing a weakened or fractured bone. FIG. 5A-D show exemplary method steps in the mixing of the two-component bone cement within the elongated body 103 in situ. FIG. 5A shows an expandable body 103 housing a powder component 122 of a bone cement. The expandable body 103 is attached to the distal end 104 of the delivery catheter 110. The powder component 122 may be pre-loaded in the expandable body 103 or added to the expandable body 103 by injection, suction, or other methods known in the art. In FIG. 5B, a liquid component 124 of the two-component bone cement is added to the expandable body 103. Once the powder component 122 and the liquid component 124 of the bone cement are together, a mixing element 150 terminating in a spinning mechanism 154 is placed through an inner lumen of the delivery catheter 110 and positioned with the expandable body 103, see FIG. 5C. The spinning mechanism 154 is turned on and the powder component 122 and liquid component 124 of the bone cement are mixed together to produce a homogenous cement material with a desired viscosity. During mixing of the powder and liquid components of the bone cement, the liquid component should be distributed equally throughout the mixture so that the mixture is uniform and possesses a uniform viscosity, consistent with the manufacturer's specifications. The mixing of the two-components causes the expandable body 103 to move from a first compact state to a second expanded state. As shown in FIG. 5D, once the bone cement is at a desired viscosity, the mixing element 150 is removed from the delivery catheter 110. In an embodiment, a vacuum is created so that the production of air bubbles is minimized. For example, a vacuum pump may be attached to the Tuohy-Borst adapter 115 located at the proximal end 102 of the delivery catheter 110. After the mixing element 150 is removed from the delivery catheter 110, the mixed bone cement is able to go through a curing cycle. A pressure sensor/gauge may be incorporated into the system for repairing a weakened or fractured bone to assist a treating physician in monitoring the procedure. Alternately, the spinning mechanism 154 of the mixing element 150 may be disengaged from the rotatable shaft 152 and remain within the expandable body 103. The mixed bone cement is then cured within the expandable body 103 and around the spinning mechanism 154. The combination of the expandable body 103, the hardened bone cement, and the spinning mechanism 154, function as a rebar-enforced IBFD 100.

Figure 6A:
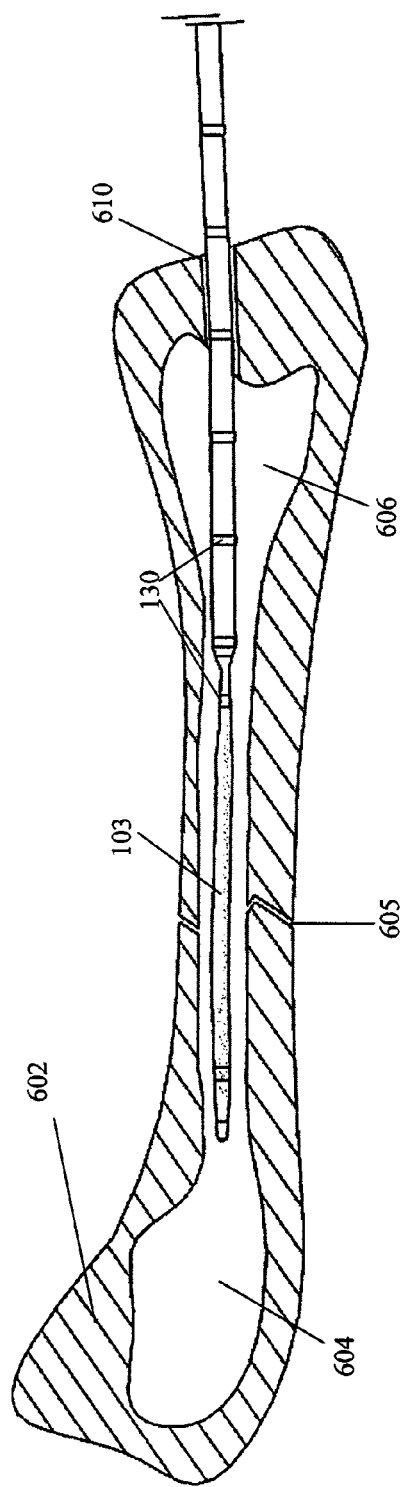
FIG. 6A and FIG. 6B show some of the method steps for utilizing a system of the presently disclosed embodiments for repair of a weakened or fractured bone.
Figure 6B:
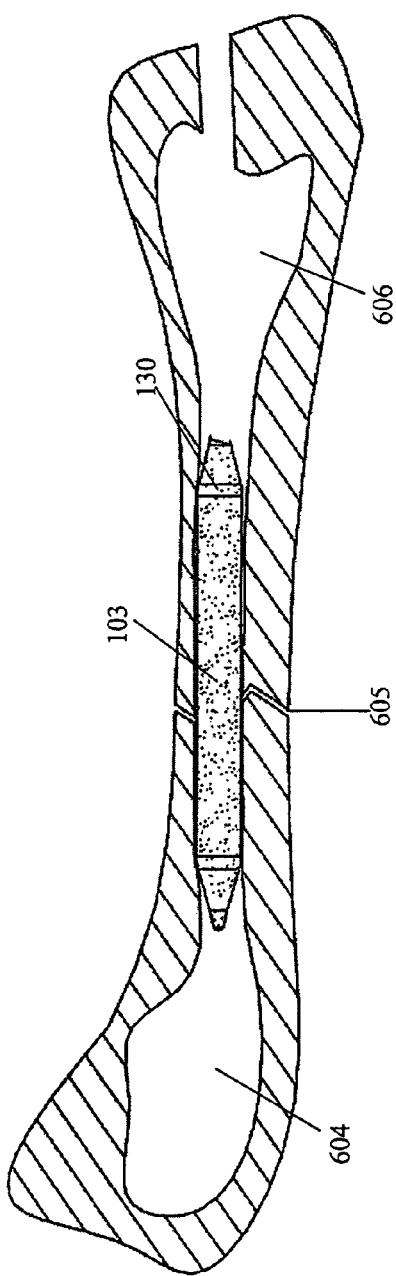

FIG. 6A and FIG. 6B illustrate close-up views of the distal end 104 of the system for repairing a weakened or fractured bone. FIG. 6A shows an internal bone fixation device (IBFD) 103 in a first compact state before a liquid component of a bone cement has been added to the IBFD 103. FIG. 6B shows the internal bone fixation device (IBFD) 103 in a second expanded state after following method steps for repairing a weakened or fractured bone. A minimally invasive incision (not shown) is made through the skin of the patient's body to expose a fractured bone 602. The incision may be made at the proximal end or the distal end of the fractured bone 602 to expose the bone surface. Once the bone 602 is exposed, it may be necessary to retract some muscles and tissues that may be in view of the bone 602. An access hole 610 is formed in the bone by drilling or other methods known in the art. In an embodiment, the access hole 610 has a diameter of about 3 mm to about 10 mm. In an embodiment, the access hole 610 has a diameter of about 3 mm.

The access hole 610 extends through a hard compact outer layer of the bone into the relatively porous inner or cancellous tissue. For bones with marrow, the medullary material should be cleared from the medullary cavity prior to insertion of the IBFD 103. Marrow is found mainly in the flat bones such as hip bone, breast bone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

A guidewire (not shown) may be introduced into the bone 602 via the access hole 610 and placed between bone fragments 604 and 606 of the bone 602 to cross the location of a fracture 605. The guidewire may be delivered into the lumen of the bone 602 and crosses the location of the break 605 so that the guidewire spans multiple sections of bone fragments. As shown, the IBFD 103, which is constructed and arranged to accommodate the guidewire, is delivered over the guidewire to the site of the fracture 605 and spans the bone fragments 604 and 606 of the bone 602. Once the IBFD 103 is in place, the guidewire may be removed. The location of the IBFD 103 may be determined using at least one radiopaque marker 130 which is detectable from the outside or the inside of the bone 602. For example, as shown in the embodiment depicted in FIG. 6, radiopaque markers 130, which are visible from outside of the body using x-ray or other detection means, are located along both the IBFD 103 and the slip sleeve 107 of the delivery catheter 110 to help align and position the system 100. Once the IBFD 103 is in the correct position within the fractured bone 602, the system 100 is attached to a delivery system which contains a bone cement. The delivery system may house both components of the bone cement, for example the powder component and the liquid component, or just the liquid component. In an embodiment, the IBFD 103 comes pre-loaded with the powder component of the bone cement. The liquid component of the bone cement is then infused through a void in the delivery catheter 110 and enters the IBFD 103 of the system 100. Once orientation of the bone fragments 604 and 606 are confirmed to be in a desired position, a mixing element terminating in a spinning mechanism is placed through an inner lumen of the delivery catheter and positioned within the IBFD 103. The spinning mechanism is turned on and the powder component and liquid component of the bone cement are mixed together to produce a homogenous cement material with a desired viscosity. The mixing of the two-components causes the expandable body 103 to move from a first compact state to a second expanded state. Once the bone cement is at a desired viscosity, the mixing element is removed from the delivery catheter. In an embodiment, a vacuum is created so that the production of air bubbles is minimized. After the mixing element is removed from the delivery catheter, the mixed bone cement is able to go through a curing cycle. Once the mixed bone cement has been hardened within the IBFD 103, the IBFD 103 may be released from the delivery catheter by known methods in the art. In an embodiment, the delivery catheter is cut to separate the IBFD 103 from the elongated shaft. A device slides over the delivery catheter and allows a right angle scissor to descend through the delivery catheter and make a cut. The location of the cut may be determined by using a fluoroscope or an x-ray. In an embodiment, the cut location is at the junction where the elongated shaft meets the IBFD 103.

In an embodiment, the system 100 is used to treat a hand or wrist fracture. The wrist is a collection of many joints and bones that allow use of the hands. The wrist has to be mobile while providing the strength for gripping. The wrist is complicated because every small bone forms a joint with its neighbor. The wrist comprises at least eight separate small bones called the carpal bones, that connect the two bones of the forearm, called the radius and the ulna, to the bones of the hand and fingers. The wrist may be injured in numerous ways. Some injuries seem to be no more than a simple sprain of the wrist when the injury occurs, but problems can develop years later. A hand fracture may occur when one of the small bones of the hand breaks. The hand consists of about 38 bones and any one of these bones may suffer a break. The palm or midhand is made up of the metacarpal bones. The metacarpal bones have muscular attachments and bridge the wrist to the individual fingers. These bones frequently are injured with direct trauma such as a crush from an object or most commonly the sudden stop of the hand by a wall. The joints are covered with articular cartilage that cushions the joints. Those skilled in the art will recognize that the disclosed device and methods can be used for to treat fractures to other bones, such as radius, ulna, clavicle, metacarpals, phalanx, metatarsals, phalanges, tibia, fibula, humerus, spine, ribs, vertebrae, and other bones and still be within the scope and spirit of the disclosed embodiments.

The presently disclosed embodiments may be used to treat a clavicle fracture, resulting in a clavicle reduction. The clavicle or collar bone is classified as a long bone that makes up part of the shoulder girdle (pectoral girdle). Present methods to affix a broken clavicle are limited. The clavicle is located just below the surface of the skin, so the potential for external fixation including plates and screws is limited. In addition, the lung and the subclavian artery reside below the collar bone so using screws is not an attractive option. Traditional treatment of clavicle fractures is to align the broken bone by putting it in place, provide a sling for the arm and shoulder and pain relief, and to allow the bone to heal itself, monitoring progress with X-rays every week or few weeks. There is no fixation, and the bone segments rejoin as callous formation and bone growth bring the fractured bone segments together. During healing there is much motion at the fracture union because there is not solid union and the callous formation often forms a discontinuity at the fracture site. A discontinuity in the collar bone shape often results from a clavicle fracture.

The presently disclosed embodiments and methods treat a clavicle fracture in a minimally invasive manner and may be used for a clavicle reduction or collar bone reduction. A benefit of using the disclosed device to repair a collar bone is the repair minimizes post repair misalignment of collar bone. A benefit of using the disclosed device to repair a clavicle is to resolve the patient's pain during the healing process.

A method for repairing a fractured bone includes gaining access to an inner cavity of the fractured bone; providing a system for use in repairing the fractured bone, the system comprising an internal bone fixation device releasably engaging a delivery catheter, the internal bone fixation device housing a powder component of a bone cement; positioning the internal bone fixation device spanning at least two bone segments of the fractured bone; adding a liquid component of the bone cement to the internal bone fixation device by passage through an inner void of the device; inserting the mixing element through the delivery catheter and into the internal bone fixation device; activating the mixing element to mix the powder component and the liquid component of the bone cement within the internal bone fixation device, wherein the internal bone fixation device moves from a first compact state to a second expanded state; removing the mixing element from the device; waiting for the mixed bone cement to cure, wherein the curing of the bone cement results in a hardened internal bone fixation device; and releasing the hardened internal bone fixation device from the delivery catheter.

A method for repairing a fractured bone includes gaining access to an inner cavity of the fractured bone; providing a system for use in repairing the fractured bone, the system comprising an internal bone fixation device releasably engaging a delivery catheter, the internal bone fixation device housing a powder component of a bone cement; positioning the internal bone fixation device spanning at least two bone segments of the fractured bone; adding a liquid component of the bone cement to the internal bone fixation device by passage through an inner void of the device; inserting a mixing element through the delivery catheter and into the internal bone fixation device, the mixing element comprising a spinning mechanism releasably engaging a rotatable shaft; activating the mixing element to mix the powder component and the liquid component of the bone cement within the internal bone fixation device, wherein the internal bone fixation device moves from a first compact state to a second expanded state; releasing the spinning mechanism from the rotatable shaft; removing the rotatable shaft from the device; waiting for the mixed bone cement to cure, wherein the curing of the bone cement results in a hardened rebar-enforced internal bone fixation device; and releasing the hardened rebar-enforced internal bone fixation device from the delivery catheter.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A system for repairing a fractured bone comprising:
   a delivery catheter having an elongated shaft with a proximal end, a distal end, and a longitudinal axis therebetween, wherein the delivery catheter has an inner void for passage of bone cement components and an inner lumen;
   an internal bone fixation device releasably engaging the distal end of the delivery catheter and adapted to move from a first compact state to a second expanded state; and
   a mixing element sized to pass through the inner lumen, the mixing element comprising a spinning mechanism releasably engaged to a distal end of a rotatable shaft, wherein the spinning mechanism is inserted into the internal bone fixation device and rotation of the rotatable shaft about a central axis rotates the spinning mechanism about the central axis so that the spinning mechanism contacts the bone cement components to mix the bone cement components together, and wherein the mixing element is sufficiently designed to disengage the spinning mechanism from the rotatable shaft.

2. The system of claim 1 further comprising an adapter releasably engaging the proximal end of the delivery catheter for receiving the mixing element and a bone cement injection system housing the bone cement components.

3. The system of claim 1 further comprising:
   a stiffening member surrounding the elongated shaft of the delivery catheter;
   a slip sleeve surrounding the stiffening member; and
   at least one radiopaque material on the delivery catheter.

4. The system of claim 2 wherein the bone cement components include a powder component and a liquid component.

5. The system of claim 4 wherein the powder component is polymethylmethacrylate powder and the liquid component is methyl methacrylate.

6. The system of claim 4 wherein the bone cement injection system carries the liquid component of the bone cement, and the powder component of the bone cement is included in the internal bone fixation device.

7. The system of claim 1 wherein the mixing element further comprises a handle attached to the rotatable shaft, wherein the handle engages a drive mechanism for rotating the rotatable shaft.

8. The system of claim 1 for use in repairing a bone fractured into at least two bone fragments.

9. The system of claim 8 wherein the internal bone fixation device is adapted to reside within an inner cavity of the at least two bone fragments and provides support to the at least two bone fragments.

10. The system of claim 9 wherein the internal bone fixation device is adapted to evenly contact a wall of the inner cavity of the at least two bone fragments when in the expanded state.

11. A system for repairing a fractured bone comprising:
   a delivery catheter having an elongated shaft with a proximal end, a distal end, and a longitudinal axis therebetween, wherein the delivery catheter has an inner void sufficiently designed for passage of a liquid component of a bone cement and an inner lumen;
   an internal bone fixation device releasably engaging the distal end of the delivery catheter, wherein the internal bone fixation device comprises a powder component of a bone cement; and
   a mixing element sized to pass through the inner lumen, the mixing element comprising a spinning mechanism having a plurality of blades extending from a rotatable shaft, wherein the plurality of blades are sufficiently designed to be positioned within the internal bone fixation device and rotation of the rotatable shaft about a central axis rotates the plurality of blades about the central axis so that the plurality of blades contact the powder component and the liquid component to mix the powder component and the liquid component together.

12. The system of claim 11 further comprising an adapter releasably engaging the proximal end of the delivery catheter for receiving the mixing element and a bone cement injection system housing the liquid component of the bone cement.

13. The system of claim 11 wherein the powder component is polymethylmethacrylate powder and the liquid component is methyl methacrylate.

14. The system of claim 11 wherein the mixing element further comprises a handle attached to the rotatable shaft, wherein the handle engages a drive mechanism for rotating the rotatable shaft.

15. The system of claim 11 for use in repairing a bone fractured into at least two bone fragments.

16. The system of claim 15 wherein the internal bone fixation device is adapted reside within an inner cavity of the at least two bone fragments and provide support to the at least two bone fragments.

17. The system of claim 15 wherein the internal bone fixation device is adapted to evenly contact a wall of the inner cavity of the at least two bone fragments when in an expanded state.

18. A system for repairing a fractured bone comprising:
   a delivery catheter having an elongated shaft with a proximal end, a distal end, and a longitudinal axis therebetween, wherein the delivery catheter has an inner void sufficiently designed for passage of a liquid component of a bone cement and an inner lumen;
   an internal bone fixation device releasably engaging the distal end of the delivery catheter, wherein the internal bone fixation device comprises a powder component of a bone cement; and
   a mixing element sized to pass through the inner lumen, the mixing element comprising a spinning mechanism engaged to a rotatable shaft, wherein the spinning mechanism has a shape and size sufficiently designed for positioning within the internal bone fixation device and rotation of the rotatable shaft about a central axis rotates the spinning mechanism about the central axis so that the spinning mechanism contacts the powder component and the liquid component to mix the powder component and the liquid component together.

19. The system of claim 18 for use in repairing a bone fractured into at least two bone fragments.

20. A system comprising:
   a delivery catheter having an elongated shaft with a proximal end, a distal end, and a longitudinal axis therebetween, wherein the delivery catheter has an inner void sufficiently designed for passage of a liquid component of a bone cement and an inner lumen;

an internal bone fixation device releasably engaging the distal end of the delivery catheter, wherein the internal bone fixation device comprises a powder component of a bone cement; and a mixing element sized to pass through the inner lumen, the mixing element comprising a plurality of wire loops joined at a distal end extending from a rotatable shaft, wherein the plurality of wire loops are sufficiently designed to be positioned within the internal bone fixation device and rotation of the rotatable shaft about a central axis rotates the plurality of wire loops about the central axis so that the plurality of wire loops contact the powder component and the liquid component to mix the powder component and the liquid component together.

* * * * *